United States Patent [19]

Jarreau et al.

[11] 4,217,280
[45] Aug. 12, 1980

[54] AMINO-3-CARDENOLIDE DERIVATIVES, PROCESS FOR THEIR PREPARATION, AND PHARMACEUTICAL COMPOSITIONS CONTAINING SAME

[75] Inventors: François-Xavier Jarreau, Versailles; Jean-Jacques Koenig, Chilly-Mazarin, both of France

[73] Assignee: Etablissements Nativelle S.A., Paris, France

[21] Appl. No.: 6,710

[22] Filed: Jan. 26, 1979

[30] Foreign Application Priority Data

Jan. 27, 1978 [FR] France ................... 78 02390

[51] Int. Cl.$^2$ ........................ C07J 19/00; A61K 31/58
[52] U.S. Cl. ............................. 260/239.57; 424/241
[58] Field of Search ................................. 260/239.57

[56] References Cited

U.S. PATENT DOCUMENTS

| 3,873,379 | 4/1975 | Stache et al. | 260/239.57 |
| 3,901,882 | 8/1975 | Meyer | 260/239.57 |

*Primary Examiner*—Elbert L. Roberts
*Attorney, Agent, or Firm*—Sughrue, Rothwell, Mion, Zinn and Macpeak

[57] ABSTRACT

Amino-3-cardenolide derivatives represented by the genral formula (I)

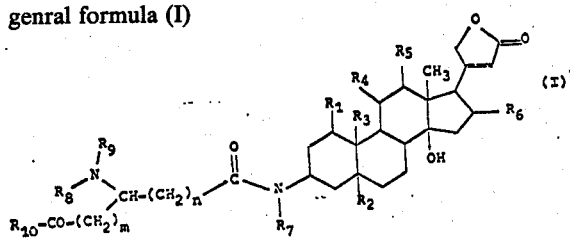

wherein n and m, which may be the same or different, each represents an integer from 0 to 4; $R_1$, $R_2$, $R_4$, $R_5$ and $R_6$, which may be the same or different, each represents a hydrogen atom or a hydroxy, alkoxy or acyloxy group; $R_3$ represents a lower alkyl, aldehyde, haloalkyl, hydroxyalkyl, acyloxyalkyl, or ethylenedioxyalkyl group; $R_7$ represents a hydrogen atom or an alkyl group; $R_8$ represents a hydrogen atom or an alkyl, acyl, alkyloxycarbonyl or aralkoxycarbonyl group; $R_9$ represents a hydrogen atom or an alkyl group; $R_8$ and $R_9$ can combine and form with the nitrogen atom a heterocyclic ring; $R_{10}$ represents a hydroxy, alkoxy or aralkoxy group, an amino residue of amino acid or of an oligopeptide, useful especially for the treatment of cardiac ailments.

13 Claims, No Drawings

AMINO-3-CARDENOLIDE DERIVATIVES, PROCESS FOR THEIR PREPARATION, AND PHARMACEUTICAL COMPOSITIONS CONTAINING SAME

BACKGROUND OF THE INVENTION

1. Field of the Invention

The present invention relates to new cardenolide derivatives, and in particular amino-amides of amino-3-cardenolides as well as their mineral or organic salts, to their preparation and to their therapeutic application.

2. Description of the Prior Art

Numerous natural substances derived from cardiotonic heterosides are used therapeutically for the treatment of cardiac incapacity. For example, it is known that the cardiotonic activity of cardenolide-glycosides such as digitoxin is particularly dependent upon the structure of the cardenolide moiety and on the nature of the sugar-containing chain at $3\beta$. However, these natural substances generally present a low therapeutic margin, which renders their utilization delicate. Hence there is interest in preparing compositions of similar structure but possessing a strong cardiotonic activity associated with low toxicity.

Thus, it was proposed to prepare cardenolide derivatives having an amino group directly attached to the carbon in the 3 position of the steroid ring starting from oxo-3 cardenolides by reaction with hydroxylamine to form the corresponding oxime which is then reduced by catalytic hydrogenolysis. Also known are other compositions obtained by attaching an appropriate substituent at the 3 position of the cardenolide moiety, for example, an amino residue. Such compositions are described in French Pat. Nos. 2,085,722 and 2,191,694.

However, the presence of the amino residue confers basic properties to these compounds.

Also cardenolide derivatives such as the esters and aminoacids of cardenolides, obtained by coupling cardiotonic genins and amino diacids, are known as described in French patent application No. 75.15462 (equivalent to U.S. Pat. No. 4,060,607).

SUMMARY OF THE INVENTION

The present invention relates to new derivatives of cardiotonic cardenolides possessing modified therapeutic activity and showing amphoteric properties providing new and original pharmacokinetic properties.

The cardenolide derivatives of the present invention are represented by the following general formula (I):

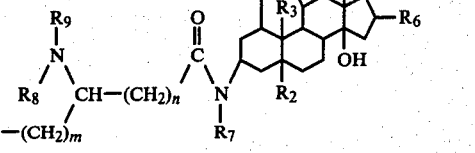

wherein m and n, which may be the same or different, each represents an integer from 0 to 4, $R_1$, $R_2$, $R_4$, $R_5$ and $R_6$, which may be the same or different, each represents a hydrogen atom or a hydroxy, alkoxy or acyloxy group; $R_3$ represents a lower alkyl, aldehyde, haloalkyl, hydroxyalkyl, acyloxyalkyl or ethylenedioxyalkyl group; $R_7$ represents a hydrogen atom or an alkyl group; $R_8$ represents a hydrogen atom or an alkyl, acyl, alkoxycarbonyl or aralkoxycarbonyl group; $R_9$ represents a hydrogen atom or an alkyl group; $R_8$ and $R_9$ can combine and form with the nitrogen atom a heterocyclic ring; $R_{10}$ represents a hydroxy, alkoxy or aralkoxy group, an amino residue of an amino acid or an oligopeptide.

The invention also provides a process for preparation of the new cardenolide derivatives of the Formula I, comprising reacting an amino-3 cardenolide at the amino functional group with an amino diacid using one of the carboxylic acid functional groups.

DETAILED DESCRIPTION OF THE INVENTION

As indicated above, the cardiotonic activity of compounds such as those represented by Formula (I) depends in particular upon the structure of the cardenolide moiety and more especially upon the stereo-chemistry of the substituents which are attached to it. The present invention preferably provides cardenolide derivatives represented by Formula (Ia) below, where the stereochemical configuration has been indicated.

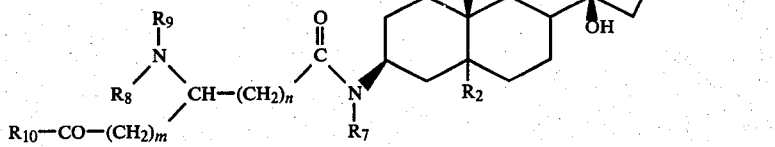

wherein $R_1$ to $R_{10}$, n and m, have the definitions given in Formula (I), $R_2$ being in $\alpha$ or $\beta$.

Among the compounds represented by Formula (Ia) above, the invention provides preferably compounds for which n has a value of 1 or 2, and m the value of 0, or the reverse, $R_1$, $R_2$ and $R_6$ represent a hydrogen atom or a hydroxy group, $R_3$ represents a lower alkyl group, for example, a methyl group, or a hydroxyalkyl group, for example a hydroxymethyl group, or an aldehyde group, $R_4$ represents a hydrogen atom and $R_5$ represents a hydrogen atom, a hydroxy group or an acetoxy group.

In Formula (Ia) shown above, $R_7$, $R_8$ and $R_9$ preferably represent a hydrogen atom or a methyl group. When $R_8$ represents an acyl group, this group can, for example, be an acetyl group, or an acyl group derived from an amino acid or from an oligo-peptide; $R_8$ can also be an alkoxy- or aralkoxycarbonyl group, and, for example, a t-butyloxycarbonyl or benzyloxycarbonyl group diversely substituted on the aromatic ring; $R_8$ and $R_9$ can be jointly two acyl residues and form a phthalimide group with the nitrogen atom to which they are attached; $R_{10}$ can represent a hydroxy group, an alkoxy group such as methoxy, ethoxy or phthalimidomethyloxy, or an aralkoxy group and, in particular, a benzyloxy group.

The invention provides in particular derivatives of amino-3 cardenolide and of aspartic or glutamic acid and the salts thereof and especially particularly the following compounds:

Compound A deoxy-3 α-L-aspartylamino-3β digitoxigenin

Compound B deoxy-3 β-L-aspartylamino-3β digitoxigenin

Compound C deoxy-3 γ-L-glutamylamino-3β digitoxigenin

Compound D deoxy-3 N-β-L-aspartyl N'-methylamino-3β digitoxigenin

Compound E deoxy-3 N-γ-L-glutamyl N'-methylamino-3β digitoxigenin

Compound F deoxy-3 β-L-aspartylamino-3β acetoxy-12β digoxigenin

Compound G deoxy-3 γ-L-glutamylamino-3β acetoxy-12β digoxigenin

As indicated previously, the amino-3 cardenolide derivatives in accordance with the present invention have the advantage of possessing properties resulting from the presence of an acid group and a basic amino group in the same molecule, which enables the preparation of salts by reaction both with bases and with mineral and organic acids.

The present invention also includes the amino-3 cardenolide amino-amide salts of the Formula (I), in particular, the pharmaceutically acceptable salts, obtained by reaction with usual acids, such as hydrochloric, sulfuric, phosphoric, acetic, propionic, oxalic, lactic, citric, tartaric, ascorbic, aspartic, glutamic or malonic acids, or with bases, such as an alkali metal hydroxide, for example, sodium, potassium or lithium hydroxide, or an alkaline earth metal hydroxide, such as magnesium or calcium hydroxide. Metal salts such as aluminum or ammonium salts can also be prepared.

The salts can be produced in the normal manner, by reacting substantially stoichiometric proportions of the amino-3 derivative in the acid or free base form with an appropriate hydroxide or acid in a solvent suitably selected in accordance with the acid or base, for example, water or an alcohol.

In accordance with the process of the invention, an amino-cardenolide, previously protected as necessary, is reacted with an amino diacid derivative appropriately substituted at the amino group and at one of the two carboxylic acid groups, the other being appropriately activated. As a starting cardenolide, for example, deoxy amino-3 digitoxigenin, deoxy amino-3 digoxigenin, deoxy amino-3 uzarigenin, etc. can be chosen. Examples of amino diacids which can be used for the preparation of the compounds of the present invention include aspartic acid, glutamic acid, amino-2 propanedioic-1,3 acid, amino-adipic acid, aminopimelic acid, etc., in levorotatory, dextrorotatory or racemic form. These various amino diacids can possibly be substituted at the nitrogen atom thereof.

The protective groupings for the amino residue and of the carboxylic acid functional group may be those normally employed in the synthesis of peptides, with examples including benzyloxycarbonyl, trityl, phthalimido, etc. groupings, for the amino residue, and benzyl or methyl ester or phthalimidomethyl groupings, etc. for the carboxylic acid functional groups.

The activation of the second carboxylic acid functional group may be effected in accordance with normal techniques of peptide synthesis, by transforming it, for example, into an acyl chloride, an active ester, an anhydride, etc., or by associating it with a condensation agent, such as, for example, dicyclohexylcarbodiimide, N,N'-carbonyldiimidazole, diethyl-phosphonyl cyanide, diphenylphosphonylazide, triphenylphosphine disulfide or a halo-2 methylpyridinum salt.

In addition, the protective groupings of the various alcohol, carboxylic acid, amino and/or aldehyde functional groups, which exist in the condensation products, may be eliminated, then possibly replaced by other groupings, using normal techniques.

Coupling is effected, preferably by adding the amino-cardenolide cold to a solution of the suitably protected and activated acid, and then allowing the reaction to occur at room temperature for a few hours. A predominant composition is formed which is extracted from the reaction medium, previously diluted with water and acidified, with an organic solvent, and which is purified by crystallization or chromatography.

Pharmacological and toxicological evaluations carried out on the compositions of the present invention demonstrate that they possess interesting properties enabling their therapeutic applications and especially in the field of application of known cardiotonic heterosides.

More specifically the compositions of the present invention possess inhibitive activity on dependent ATPase $Na^+$, $K^+$ and inotropic activity.

The inhibitive activity on dependent ATPase $Na^+$, $K^+$ has been verified on rat brain tissue. The inotropic activity has been tested on an isolated and perfused (Langendorff type) guinea pig heart and in situ on dog heart. These experiments show that the compounds of the present invention possess properties analogous to those of known cardiotonic heterosides, while possessing a peptide residue at the 3 position of the steroid ring, by bringing about an increase in myocardium contraction and in addition bringing out other differences at the level of pharmacological parameters as well as an interesting therapeutic margin.

The active doses, administered intravenously in a dog, are less than 1 mg/kg of weight.

These pharmacological properties demonstrate that the compounds of the present invention are especially recommended for the treatment of cardiac ailments, and in particular cardiac insufficiency and rhythm problems.

The new compounds of the present invention can be administered in the usual forms containing a pharmacologically effective amount of the compound as an active ingredient along with pharmaceutically acceptable supports, for example, in the form of tablets, gelules, capsules, pills, suppositories, injectable solutions or syrups.

As a solid diluant for the preparation of tablets, lactose, mannitol, sorbitol, starch, polyvinylpyrrolidone, magnesium or aluminum stearate, cellulose powder, colloidal silica, talc, etc., may be used.

Injectable solutions may be prepared using diluants such as double distilled water, propylene glycol, a hydroalcoholic solution, or a mixture of these diluants, preferably in the presence of an appropriate preservative selected from those normally used in the art.

Orally ingestible forms can also be prepared, for example, solutions containing the compound of the present invention dissolved in water and glycerol in the presence of a sweetening agent and an antioxidant, or suspensions of the compound of the present invention in an aqueous solution of saccharose in the presence of a thickener, a sweetening agent and an antioxidant.

All formulations adapted to various types of administration, i.e., orally, parenterally, or rectally, can be used, the compound of this invention being present as the active ingredient with suitably selected acceptable pharmaceutical excipients.

For example, the following formulations may be cited:

| A - Compound A | 0.25 | mg |
|---|---|---|
| Lactose | 134.75 | |
| Talc | 15.0 | |
| | 150.0 | mg |
| B - Compound D | 0.25 | mg |
| Starch | 81.25 | |
| Colloidal Silica | 0.50 | |
| Microcrystalline Cellulose | 18.00 | |
| | 100.0 | mg |
| Injectable Solution: | | |
| Compound A | 0.01 | mg |
| Preservative | 0.0001 | |
| Water (quantity sufficient for) | 1.0 | ml |
| Orally Ingestible Solution: | | |
| Compound D | 0.25 | mg |
| Sweetening Agent | 2.0 | |
| Glycerol | 30.0 | |
| Antioxidant | 0.01 | |
| Water (quantity sufficient for) | 100.0 | ml |

The dosage may vary in accordance with the subject being treated and the affliction in question, the doses administered daily being generally on the order of between 0.01 and 1 mg for oral administration in man.

The following examples are given to illustrate the present invention but are not to be construed to limit the scope of the invention.

EXAMPLE 1

Deoxy-3 α-(N-benzyloxycarbonyl, β-benzyl)-(L)-aspartylamino-3β digitoxigenin 270 mg of deoxy-3 amino-3β digitoxigenin and 165 mg of dicyclohexylcarbodiimide was placed in solution with 10 ml of methylene chloride at 0°. 297 mg of N-benzyloxycarbonyl-β-benzyl-(L)-aspartic acid in a solution of 10 ml of methylene chloride was added to that solution, drop by drop, with agitation at 0° C. After a few minutes a white precipitate appeared. At the end of an hour the reaction had terminated and the residue was filtered, evaporated to dryness and dissolved in 20 ml of benzene. The benzene fraction was washed three times, with 10 ml of N-hydrochloric acid, with water, with a solution of sodium bicarbonate and finally with water. The aqueous fractions were again extracted twice with 10 ml of benzene. The benzene fractions were dried and evaporated to dryness, dissolved in a benzene/ether (1/1) mixture, filtered and the filtrate was evaporated to dryness. The residue was composed of 540 mg of deoxy-3 α-(N-benzyloxycarbonyl, β-benzyl)-(L)-aspartylamino-3β digitoxigenin (yield=96%).

IR spectrum (Nujol): 3480, 3340, 1780, 1755, 1740, 1665, 1620 and 1530 cm$^{-1}$.

TLC: (CH$_2$Cl$_2$/MeOH—95/5): Rf=0.47.

EXAMPLE 2

Deoxy-3 α-L-aspartylamino-3β digitoxigenin (Compound A)

500 mg of deoxy-3α(N-benzyloxycarbonyl β-benzyl)-L-aspartylamino-3β digitoxigenin was hydrogenated in solution in 80 ml of methanol, in the presence of 150 mg of palladium at 5% on calcium carbonate, for 4.5 hours (the catalyst was renewed once). The residue (333 mg) was filtered, evaporated to dryness and crystallized in pure ethanol. 248 mg of deoxy-3α-L-aspartylamino-3β digitoxigenin crystals was obtained, Compound A (yield=75%).

Melting point: m.p. (Kofler): 235°–245° (dec).

IR spectrum (Nujol) ν: 3520, 3275, 3080, 1792, 1757 1726, 1716, 1660, 1630, 1620 and 1565 cm$^{-1}$.

NMR spectrum (CD$_3$OD): δ=0.88 and 1.00 (2 s, CH$_3$), 1.70 (3H), 4.18 (2H), 4.99 (2H, 5.92 (1H) ppm.

TLC: (CHCl$_3$/EtOH/NH$_4$OH—60/45/15: Rf=0.58.

Hydrochloride of Compound A

This hydrochloride was obtained in the usual manner by reacting hydrochloric acid with Compound A, in stoichiometric proportions.

IR spectrum (Nujol) ν: 3370, 3210, 3050, 1780, 1765 1735, 1678, 1620 and 1550 cm$^{-1}$.

EXAMPLE 3

Deoxy-3 β-(N-benzyloxycarbonyl,α-benzyl)-L-aspartylamino-3β digitoxigenin

A solution of 430 mg of (N-benzyloxycarbonyl-α-benzyl)-L-aspartic acid, in 15 ml of methylene chloride, was added drop by drop to a solution, under agitation at 0°, of 360 mg of deoxy-3 amino-3β digitoxigenin and 227 mg of dicyclohexylcarbodiimide in 15 ml of methylene chloride. After reaction at 4° C. for one night, the bicyclohexylurea precipitate was filtered and the filtrate was evaporated to dryness. The residue was dissolved in an ethyl acetate/benzene mixture (1/1), the insoluble fraction was filtered out and the filtrate was washed with 1 N hydrochloric acid, water, a sodium bicarbonate solution, and finally with water. The organic phase was dried and evaporated to dryness. The residue (757 mg) was composed of deoxy-3 β-(N-benzyloxycarbonyl-α-benzyl)-L-aspartylamino-3β digitoxigenin, containing a small amount of bicyclohexylurea (yield=100%).

IR spectrum (Nujol) ν: 3340, 1780, 1755, 1740, 1655, 1535 and 1500 cm$^{-1}$.

TLC: (CH$_2$Cl$_2$/MeOH—95/5) Rf=0.4.

EXAMPLE 4

Deoxy-3 β-L-aspartylamino-3β-digitoxigenin (Compound B)

Hydrogenolysis of 600 mg of deoxy-3-β(N-benzyloxycarbonyl-α-benzyl)-L-aspartylamino-3-β digitoxigenin (i.e., the product of Example 3) in solution in 120 ml of methanol, in the presence of 150 mg of palladium at 5% on calcium carbonate for 90 minutes, gave, after filtration, evaporation to dryness and crystallization of the residue (413 mg) in ethanol, 362 mg of deoxy-3β-L-aspartylamino-3β digitoxigenin, Compound B (yield=86%).

m.p. (Kofler): 260°-264° C. (dec.)

IR spectrum (Nujol) ν: 3450, 3340, 3145, 3065, 1745, 1650, 1620, 1573, and 1510 cm$^{-1}$.

Hydrochloride of Compound B

IR spectrum (Nujol) ν: 3360, 3250, 3050, 1780, 1755, 1740, 1642, 1627, and 1550 cm$^{-1}$.

TLC: (CHCl$_3$/EtOH/NH$_4$OH—50/45/15) Rf=0.44

EXAMPLE 5

Deoxy-3 γ-(N benxyloxycarbonyl-α-benzyl)-L-glutamyl-amino-3β digitoxigenin

A solution of 430 mg of(N-benzyloxycarbonyl-α-benzyl)-L-glutamic acid, in solution in 15 ml of methylene chloride, was added drop by drop to a solution of 360 mg of deoxy-3 amino-3β digitoxigenin and 277 mg of dicyclohexylcarbodiimide in 15 ml of methylene chloride, under agitation at 0°. After reaction at 4° C. for 7 hours, it was filtered and the filtrate was evaporated to dryness. The residue (860 mg) was dissolved in ethyl acetate, the filtrate was filtered and washed successively with 1 N hydrochloric acid, water, a solution saturated with sodium bicarbonate, and finally water. The organic phase was dried and evaporated to dryness, the residue (732 mg) was composed of deoxy-3 γ(N-benzyloxycarbonyl-α-benzyl)-L-glutylamino-3β digitoxigenin, containing a small amount of bicyclohexylurea (yield=100%).

IR (Nujol): 3480, 3340, 3190, 1780, 1755, 1740, 1720, 1660, 1535 cm$^{-1}$.

TLC (CH$_2$Cl$_2$/MeOH—95/5): Rf=0.33.

EXAMPLE 6

Deoxy-3 γ-L-glutylamino-3β digitoxigenin (Compound C)

Hydrogenolysis of 548 mg of deoxy-3 γ(N-benzyloxycarbonyl-α-benzyl)-L-glutamylamino-3β digitoxigenin obtained as indicated in Example 5, in solution in 100 ml of methanol in the presence of 135 mg of palladium at 5% on calcium carbonate, for three hours (the catalyst being renewed once), gave, after filtration, evaporation to dryness and crystallization of the residue (384 mg) in an ethanol/propanol-2 mixture (50/50), 240 mg of deoxy-3 γ-L-glutamylamino-3β digitoxigenin, Compound C (yield=65%).

M.P. (Kofler): 208°-210° C. (dec.)

IR spectrum (Nujol): 3520, 3340, 3280, 3190, 3080, 1790, 1755, 1738, 1730, 1635, 1548 cm$^{-1}$.

NMR spectrum (CD$_3$OD): δ=0.87 and 0.97 (2 s, CH$_3$), 2.03 (2H), 2.75 (1H), 3.58 (1H), 4.05 (1H), 5.87 (S,1H) ppm.

TLC (CHCl$_3$/EtOH/NH$_4$OH—50/45/15): Rf=0.47.

Hydrochloride of Compound C

IR spectrum (Nujol): 3350, 1780, 1755, 1740, 1625, 1542 cm$^{-1}$.

EXAMPLE 7

Deoxy-3 N-β-(N-benzyloxycarbonyl-α-benzyl)-L-aspartyl N'-methylamino-3β digitoxigenin A solution of 350 mg of (N-benzyloxycarbonyl-α-benzyl)-L-aspartic acid in 15 ml of methylene chloride was added drop by drop to a solution, under agitation at 0°, of 319 mg of deoxy-3 N-methylamino-3β digitoxigenin and 185 mg of dicyclohexylcarbodiimide in 15 ml of methylene chloride. After reaction at 4° C. for 5 hours, this was filtered and the filtrate was evaporated to dryness. The residue was dissolved in ethyl acetate, the insoluble material was filtered off and the filtrate was washed with 1 N hydrochloric acid, water, a saturated solution of sodium bicarbonate, and finally with water. The organic phase was dried and evaporated to dryness and the residue (605 mg) was washed several times with hexane. The insoluble material (572 mg) was composed of deoxy-3 N-β-(N-benzyloxycarbonyl-α-benzyl)-L-aspartyl N'-methylamino-3β digitoxigenin (yield=95%).

IR spectrum: (Nujol): 3430, 1780, 1755, 1745, 1630, 1495 cm$^{-1}$.

TLC: (CH$_2$Cl$_2$/MeOH—97.5/2.5, NH$_3$ atmosphere), Rf=0.53.

EXAMPLE 8

Deoxy-3 N-β-L-aspartyl N'-methylamino-3β digitoxigenin (Compound D)

Hydrogenolysis of 480 mg of deoxy-3 N-β(N-benzyloxycarbonyl-α-benzyl)-L-glutamylamino3β digitoxigenin in solution in 50 ml of methanol, in the presence of 120 mg of palladium at 5% on calcium carbonate for 3 hours (the catalyst being renewed once) gave, after filtration and evaporation to dryness, 60 mg of a white crystalline residue. The filtrate and insoluble material were extracted several times with boiling methanol, this was filtered hot and evaporated to dryness. The second residue (240 mg), combined with the first, was washed with boiling ethanol. This gave 161 mg of deoxy-3 N-β-L-aspartyl N'-methylamino-3β digitoxigenin Compound D (yield=48%).

M.P. Kofler: 202°-204° C.

IR spectrum (Nujol) ν: 3290, 3175, 1745, 1655, 1637, 1618 cm$^{-1}$.

TLC (CHCl$_3$/EtOH/NH$_4$OH 60/45/15) Rf=0.43.

Hydrochloride of Compound D

IR spectrum (Nujol) ν: 3400, 3160, 1780, 1755, 1625 cm$^{-1}$.

NMR spectrum (CD$_3$OD): δ=0.85 and 1.07 (2s, CH$_3$), 2.55 (1H), 3.02 (CH$_3$), 2.6 to 3.2 (3H), 4.27 (1H), 5.92 (1H) ppm.

EXAMPLE 9

Deoxy-3 N-γ-(N-benzyloxycarbonyl-α-benzyl)-L-glutamyl N'-methylamino-3β digitoxigenin A solution of 356 mg of (N-benzyloxycarbonyl-α-benzyl)-L-glutamic acid in solution in 15 ml of methylene chloride was added drop by drop to a solution, under agitation at 0° C., of 308 mg of deoxy-3 methylamino-3β digitoxigenin and 182 mg of dicyclohexylcarbodiimide in 15 cm$^3$ of methylene chloride.

After reaction at 4° C. for 24 hours, this was filtered and evaporated to dryness. The residue was dissolved in ethyl acetate, washed in 1 N hydrochloric acid, water, a saturated solution of sodium bicarbonate, and finally water. After extraction of the aqueous phases three times with ethyl acetate in the same manner, the organic phases were dried and evaporated to dryness. The residue (693 mg) was washed several times with hexane. The insoluble material (516 mg) was composed of deoxy-3 N-γ-(N-benzyloxycarbonyl,α-benzyl)-L-glutamyl, N'-methylamino-3β digitoxigenin (yield=86%).

IR (Nujol) $\nu$: 3430, 3300, 1780, 1755, 1740, 1725, 1620, 1525, 1495 cm$^{-1}$.

TLC: ($CH_2Cl_2$/-MeOH—97.5/2.5, $NH_3$ atmosphere) Rf=0.37.

EXAMPLE 10

Deoxy-3 N-γ-L-glutamyl, N'-methylamino-3β digitoxigenin (Compound E)

Hydrogenolysis of 560 mg of deoxy-3 N-γ-(N-benzyloxycarbonyl-α-benzyl)-L-glutamyl N'-methylamino-3β digitoxigenin in solution in 50 ml of methanol in the presence of 120 mg of palladium at 5% on calcium carbonate for 4 hours (the catalyst being renewed once), gave, after filtration, evaporating the filtrate to dryness and crystallization twice of the residue (356 mg) in a mixture of propanol-2 and ethyl acetate and washing the crystals in ether, 156 mg of deoxy-3 N-γ-L-glutamyl, N'-methylamino-3β digitoxigenin, Compound E (yield=40%).

M.P. (Kofler): 188°–192° C. (dec.).

IR spectrum (Nujol) $\nu$: 3430, 1780, 1755, 1745, 1720, 1620 cm$^{-1}$.

NMR spectrum ($CD_3OD$) δ: 0.88–1.00 and 3.0 (3s,$CH_3$), 2.3 to 2.9 (3H) 3.9 (1H), 4.45 (1H), 5.87 (1H) ppm.

TLC: ($CHCl_3$/EtOH/$NH_4OH$, 60/45/15) Rf=0.4.

EXAMPLE 11

Deoxy-3 β(N-benzyloxycarbonyl,α-benzyl)-L-aspartylamino-3β acetoxy-12β digoxigenin A solution of 430 mg of (N-benzyloxycarbonyl,α-benzyl)-L-aspartic acid in 15 ml of methylene chloride was added drop by drop to a solution, under agitation at 0°, of 430 mg of deoxy-3 amino-3β acetoxy 12β digoxigenin and 227 mg of dicyclohexylcarbodiimide in 15 ml of methylene chloride. After reaction at 4° C. for 8 hours, the precipitate was filtered and the filtrate evaporated to dryness. The residue was dissolved in ethyl acetate, the insoluble material was filtered and the filtrate washed with 1 N hydrochloric acid, water, a solution of sodium bicarbonate and finally water. After drying and evaporating the organic phase to dryness, the residue (812 mg) was dissolved several times in a hot ethyl acetate-benzene mixture (1/1). This was filtered and the filtrate was evaporated to dryness. The residue (767 mg) was composed of deoxy-3β-(N-benzyloxycarbonyl,α-benzyl)-L-aspartylamino-3β-acetoxy-12β digoxigenin (yield=100%).

IR (Nujol) $\nu$: 3460, 3340, 1790, 1755, 1740, 1650, 1620, 1530 cm$^{-1}$.

TLC: ($CH_2Cl_2$/MeOH, 95/5) Rf=0.38

EXAMPLE 12

Deoxy-3 β-L-aspartylamino-3β acetoxy-12β digoxigenin (Compound F)

Hydrogenolysis of 655 mg of deoxy-3 β(N-benzyloxycarbonyl, α-benzyl)-L-aspartylamino-3β acetoxy-12β digoxigenin in solution in 50 ml of methanol in the presence of 160 mg of palladium at 5% on calcium carbonate for 4 hours gave, after filtration, evaporation of the filtrate to dryness and crystallization twice of the residue (470 mg) in pure ethanol, 327 mg of deoxy-3 β-L-aspartylamino-3β acetoxy-12β digoxigenin crystals, Compound F (yield=70%).

M.P. Kofler: 234°–260° C. (dec.)

IR spectrum (Nujol) $\nu$: 3420, 3250, 1780, 1765, 1730, 1640, and 1550 cm$^{-1}$.

NMR spectrum ($CD_3OD$) δ: 0.88–1.00 and 2.08 (3s, $CH_3$), 2.87 (1H), 2.96 (2H), 4,08 (1H), 4.35 (1H), 5.10 (1H), 5.93 (1H) ppm.

TLC: ($CHCl_3$/EtOH/$NH_4OH$, 60/45/15) Rf=0.4.

EXAMPLE 13

Deoxy-3 γ(N-benzyloxycarbonyl,α-benzyl)-L-glutamylamino-3β acetoxy-12β digoxigenin A solution of 445 mg of (N-benzyloxycarbonyl,α-benzyl)-L-glutamic acid in solution in 15 ml of methylene chloride was added drop by drop to a solution, under agitation at 0° of 430 mg of deoxy-3 amino-3β acetoxy-12β digoxigenin and 227 mg of dicyclohexylcarbodiimide in 15 ml of methylene chloride. After reaction at 4° C. for 1 night, it was filtered and the filtrate was evaporated to dryness. The residue (896 mg) was dissolved in an ethyl acetate-benzene mixture (1/1), the insoluble material was filtered and the filtrate washed with 1 N hydrochloric acid, water, a solution of sodium bicarbonate, and finally water. The organic phase was dried and evaporated to dryness. The residue (793 mg) was composed of deoxy-3 γ-(N-benzyloxycarbonyl,α-benzyl)-L-aspartylamino-3β acetoxy-12β digoxigenin (yield=100%).

IR (Nujol): 3480, 3350, 1780, 1755, 1730, 1650, 1630, and 1525 cm$^{-1}$.

TLC: ($CH_2Cl_2$/MeOH, 95/5) Rf=0.34.

EXAMPLE 14

Deoxy-3 γ-L-glutamylamino-3β acetoxy-12β digoxigenin (Compound G)

Hydrogenalysis of 680 mg of deoxy-3 γ-(N-benzyloxycarbonyl α-benzyl)-L-glutamylamino-3β acetoxy-12β digoxigenin in 60 ml of methanol in the presence of 165 mg of palladium at 5% on calcium carbonate for 5 hours gave, after filtration, evaporation of the filtrate to dryness, washing of the residue (503 mg) in ethyl acetate and crystallization by trituration in ether, 320 mg of deoxy-3 γ-L-glutamylamino-3β acetoxy-12β digoxigenin, Compound G (yield=67%).

M.P. (Kofler): 195°–210° (dec.)

IR spectrum (Nujol) $\nu$: 3510, 3360, 1780, 1765, 1730, 1630, 1540 cm$^{-1}$.

NMR spectrum ($CD_3OD$): δ: 0.92–0.99–2.10 (3s,$CH_3$), 2.82 (1H), 1.1 (1H), 4.5 (1H), 5.04 (1H) 5.92 (1H) ppm.

What is claimed is:

1. Cardenolide derivatives represented by the general formula I

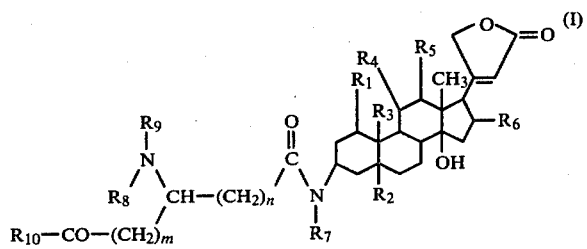

wherein m and n, which may be the same or different, each represents an integer from 0 to 4; $R_1$, $R_2$, $R_4$, $R_5$ and $R_6$, which may be the same or different, each represents a hydrogen atom or a hydroxy, alkoxy or acyloxy group; $R_3$ represents a lower alkyl, aldehyde, haloalkyl, hydroxyalkyl, acyloxyalkyl or ethylenedioxyalkyl group; $R_7$ represents a hydrogen atom or an alkyl group; $R_8$ represents a hydrogen atom or an alkyl, acyl, alkyloxycarbonyl or aralkoxycarbonyl group; $R_9$ represents a hydrogen atom or an alkyl group; $R_8$ and $R_9$ can combine with the nitrogen atom and form a heterocyclic ring; $R_{10}$ represents a hydroxy, alkoxy, or aralkoxy group, an amino acid group or an oligopeptide group bonded through the nitrogen atom of said amino acid group or of said oligopeptide group; and basic mineral and organic acid salts thereof.

2. The cardenolide derivatives of claim 1, wherein $R_1$, $R_2$ and $R_6$ represent a hydrogen atom or a hydroxy group; $R_3$ represents a methyl, hydroxymethyl or aldehyde group; $R_4$ represents a hydrogen atom; $R_5$ represents a hydrogen atom, or a hydroxy or acetoxy group.

3. The cardenolide derivatives of claim 1, wherein $R_7$ and $R_9$ represent a hydrogen atom or a methyl group; $R_8$ represents a hydrogen atom, a methyl group or an alkoxycarbonyl or aralkoxycarbonyl group; $R_{10}$ represents a hydroxy, alkoxy or aralkoxy group.

4. The cardenolide derivatives of claim 1, 2 or 3, wherein n is 1 or 2 and m is 0.

5. The cardenolide derivatives of claim 1, 2 or 3, wherein n is 0 and m is 1 or 2.

6. The cardenolide derivatives of claim 1, selected from the group consisting of deoxy-3-α-L-aspartylamino-3β-digitoxigenin, deoxy-3 β-L-aspartylamino-3β-L-aspartylamino-3β-digitoxigenin, deoxy-3 γ-L-glutylamino-3β digitoxigenin, deoxy-3-N-β-L-aspartyl-N'-methylamino-3β digitoxigenin, deoxy-3 N-γ-L-glutamyl N'-methylamino-3β digitoxigenin, deoxy-3 β-L-aspartylamino-3β-acetoxy-12β digoxigenin, or deoxy-3 γ-L-glutylamino-3β acetoxy-12β digoxigenin.

7. A pharmaceutical composition comprising, as an active ingredient, a cardenolide derivative of claim 1 with one or more pharmaceutically acceptable carriers or diluents.

8. A process for preparation of aminocardenolides of claim 1, comprising reacting an aminocardenolide previously protected with an amino diacid derivative suitably substituted at the amino functional group, and at one of the two carboxylic acid functional groups thereof, the other of said carboxylic acid functional groups being activated, and, if necessary, removing the protective groups and, if necessary, forming a salt thereof.

9. The process of claim 8, wherein the reaction is carried out at room temperature.

10. Cardenolide derivatives represented by the general formula I

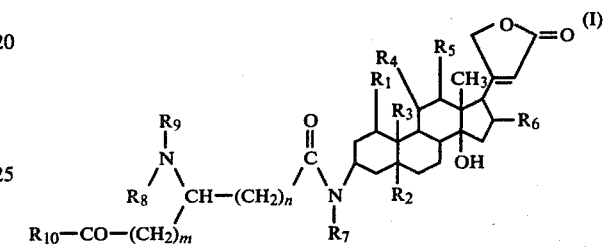

wherein m and n, which may be the same or different, each represents an integer from 0 to 4; $R_1$ and $R_2$ represent a hydrogen atom or a hydroxy group; $R_3$ represents a methyl, hydroxy methyl or aldehyde group; $R_4$ represents a hydrogen atom; $R_5$ represents a hydrogen atom, or a hydroxy or acetoxy group; $R_6$ represents a hydrogen atom or a hydroxy group; $R_7$ represents a hydrogen atom or a methyl group; $R_8$ represents a hydrogen atom, a methyl group or an alkoxycarbonyl or aralkoxycarbonyl group; $R_9$ represents a hydrogen atom or a methyl group; $R_{10}$ represents a hydroxy, alkoxy or aralkoxy group.

11. The process of claim 8, wherein the amino diacid derivative is a derivative of an amino diacid selected from the group consisting of aspartic acid, glutamic acid, amino-2-propanedioic-1,3 acid, aminoadipic acid and aminopimelic acid.

12. The process of claim 8, wherein the process includes removing any protective group present.

13. The process of claim 12, wherein the process includes forming a salt thereof after removal of any protective group.

* * * * *